(12) United States Patent
Bedenbaugh

(10) Patent No.: US 9,314,614 B2
(45) Date of Patent: *Apr. 19, 2016

(54) LEAD AND METHODS FOR BRAIN MONITORING AND MODULATION

(71) Applicant: BOSTON SCIENTIFIC NEUROMODULATION CORPORATION, Valencia, CA (US)

(72) Inventor: Purvis Bedenbaugh, Tampa, FL (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/665,533

(22) Filed: Oct. 31, 2012

(65) Prior Publication Data

US 2013/0197424 A1 Aug. 1, 2013

Related U.S. Application Data

(63) Continuation of application No. 11/828,547, filed on Jul. 26, 2007, now Pat. No. 8,321,025.

(60) Provisional application No. 60/820,919, filed on Jul. 31, 2006.

(51) Int. Cl.
*A61N 1/05* (2006.01)

(52) U.S. Cl.
CPC ............ *A61N 1/0529* (2013.01); *A61N 1/0534* (2013.01); *A61N 1/0536* (2013.01)

(58) Field of Classification Search
CPC ........................... A61N 1/0529; A61N 1/0536
USPC ............... 600/373, 378, 393; 607/45, 46, 116
See application file for complete search history.

(56) References Cited

U.S. PATENT DOCUMENTS

| 4,044,774 A | 8/1977 | Corbin et al. |
| 4,602,624 A | 7/1986 | Naples et al. |

(Continued)

FOREIGN PATENT DOCUMENTS

| EP | 0580928 A1 | 2/1994 |
| EP | 0650694 B1 | 7/1998 |

(Continued)

OTHER PUBLICATIONS

Baldi et al., "A Microstructured Silicon Membrane with Entrapped Hydrogels for Environmentally Sensitive Fluid Gating," Sensor and Actuators B, 114(1):9-18, 2006.

(Continued)

*Primary Examiner* — Tammie K Heller
(74) *Attorney, Agent, or Firm* — Lowe Graham Jones PLLC; Bruce E. Black

(57) ABSTRACT

An apparatus, a system and methods for modulating and monitoring tissue have an elongate member with proximal and distal ends and a plurality of annular stimulating electrodes axially arranged along the elongate member. The stimulating electrodes are disposed near the distal end and are adapted to pass current into tissue. At least one of the annular stimulating electrodes has at least three independent stimulation points on the electrode. The apparatus also includes a plurality of recording electrodes that are adapted to measure local tissue potentials and a plurality of conductors are coupled with the recording and stimulating electrodes. An optional multiple contact connecting terminal may be coupled with the conductors and is disposed near the proximal end of the elongate member.

18 Claims, 9 Drawing Sheets

(56) References Cited

U.S. PATENT DOCUMENTS

| | | |
|---|---|---|
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,405,375 A | 4/1995 | Ayers et al. |
| 5,458,629 A | 10/1995 | Baudino et al. |
| 5,522,874 A | 6/1996 | Gates |
| 5,683,422 A | 11/1997 | Rise |
| 5,711,316 A | 1/1998 | Elsberry et al. |
| 5,713,922 A | 2/1998 | King |
| 5,716,377 A | 2/1998 | Rise |
| 5,800,350 A | 9/1998 | Coppleson et al. |
| 5,843,148 A | 12/1998 | Gijsbers et al. |
| 5,891,084 A | 4/1999 | Lee |
| 5,938,688 A | 8/1999 | Schiff |
| 5,987,361 A | 11/1999 | Mortimer |
| 6,011,996 A | 1/2000 | Gielen et al. |
| 6,018,684 A | 1/2000 | Bartig et al. |
| 6,038,480 A | 3/2000 | Hrdlicka et al. |
| 6,094,598 A | 7/2000 | Elsberry et al. |
| 6,128,537 A * | 10/2000 | Rise .............................. 607/45 |
| 6,134,478 A | 10/2000 | Spehr |
| 6,161,047 A | 12/2000 | King et al. |
| 6,167,311 A | 12/2000 | Rezai |
| 6,227,203 B1 | 5/2001 | Rise et al. |
| 6,301,492 B1 | 10/2001 | Zonenshayn |
| 6,322,559 B1 | 11/2001 | Daulton et al. |
| 6,475,750 B1 | 11/2002 | Han et al. |
| 6,484,057 B2 | 11/2002 | Ideker et al. |
| 6,510,347 B2 | 1/2003 | Borkan |
| 6,529,774 B1 | 3/2003 | Greene |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 6,997,922 B2 | 2/2006 | Theeuwas et al. |
| 7,006,872 B2 | 2/2006 | Gielen et al. |
| 7,010,356 B2 | 3/2006 | Jog et al. |
| 7,027,852 B2 | 4/2006 | Helland |
| 7,047,082 B1 | 5/2006 | Schrom et al. |
| 7,047,084 B2 | 5/2006 | Erickson et al. |
| 7,051,419 B2 | 5/2006 | Schrom et al. |
| 7,146,222 B2 | 12/2006 | Boling |
| 7,174,213 B2 | 2/2007 | Pless |
| 7,181,288 B1 | 2/2007 | Rezai et al. |
| 7,292,890 B2 | 11/2007 | Whitehurst et al. |
| 7,305,268 B2 | 12/2007 | Gliner et al. |
| 7,337,005 B2 | 2/2008 | Kim et al. |
| 7,346,382 B2 | 3/2008 | McIntyre et al. |
| 7,489,971 B1 | 2/2009 | Franz |
| 7,617,006 B2 | 11/2009 | Metzler et al. |
| 7,668,601 B2 | 2/2010 | Hegland et al. |
| 7,676,273 B2 | 3/2010 | Goetz et al. |
| 7,761,985 B2 | 7/2010 | Hegland et al. |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,583,237 B2 | 11/2013 | Bedenbaugh |
| 2001/0023368 A1 | 9/2001 | Black et al. |
| 2002/0062143 A1 | 5/2002 | Baudino et al. |
| 2002/0156513 A1 | 10/2002 | Borkan |
| 2002/0183817 A1 | 12/2002 | Van Venrooij et al. |
| 2003/0195602 A1 | 10/2003 | Boling |
| 2003/0220676 A1 * | 11/2003 | Helland .......................... 607/122 |
| 2004/0015205 A1 | 1/2004 | Whitehurst et al. |
| 2004/0039434 A1 | 2/2004 | Schrom et al. |
| 2004/0267328 A1 | 12/2004 | Duffin et al. |
| 2005/0015130 A1 | 1/2005 | Gill |
| 2005/0038489 A1 | 2/2005 | Grill |
| 2005/0171587 A1 | 8/2005 | Daglow et al. |
| 2005/0222642 A1 | 10/2005 | Przybyszewski et al. |
| 2005/0246004 A1 | 11/2005 | Cameron et al. |
| 2005/0246006 A1 | 11/2005 | Daniels |
| 2006/0004422 A1 | 1/2006 | De Ridder |
| 2006/0025841 A1 | 2/2006 | McIntyre |
| 2006/0041284 A1 * | 2/2006 | Cameron et al. ............... 607/45 |
| 2006/0047325 A1 | 3/2006 | Thimineur et al. |
| 2006/0247697 A1 | 11/2006 | Sharma et al. |
| 2006/0247749 A1 * | 11/2006 | Colvin .......................... 607/116 |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2007/0225674 A1 | 9/2007 | Molnar et al. |
| 2007/0255373 A1 | 11/2007 | Metzler et al. |
| 2008/0004674 A1 | 1/2008 | King et al. |
| 2008/0004675 A1 | 1/2008 | King et al. |
| 2008/0046036 A1 | 2/2008 | King et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0204192 A1 | 8/2009 | Carlton et al. |
| 2009/0204193 A1 | 8/2009 | Kokones et al. |
| 2010/0023089 A1 | 1/2010 | DiLorenzo |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0109254 A1 | 5/2013 | Klardie et al. |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |

(56) References Cited

FOREIGN PATENT DOCUMENTS

| WO | 0158520 A1 | 8/2001 |
|---|---|---|
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

Baldi et al.,"A Hydrogel-Actuated Environmentally Sensitive Microvalve for Active Flow Control," Journal of Microelectromechanical Systems, 12(5):613-621, 2003.
Bashir et al., "Micromechanical Cantilever as an Ultrasensitive pH Microsensor,"Applied Physics Letters, 81(16):3091-3093, 2002.
Cheung, et al. Tinnitus modulation by deep brain stimulation in locus of caudate neurons (area LC). Neuroscience. Sep. 15, 2010; 169(4):1768-1778.
European search report and search opinion dated Nov. 30, 2009 for EP 07799919.1.
International search report and written opinion dated Aug. 15, 2008 for PCT/US2007/074746.
Krsko et al, "Biointeractive Hydrogels," Materials Today, 8(12):36-44, Dec. 2005.
Seigel, "Hard/Soft Microfabrication for Biosensing and Drug Delivery," University of Minnesota Nanotechnology Presentation, 9 pages total. Downloaded from Internet: <<http://www.business.umn.edu/documents/RonSiegel.pdf.
Steege et al., "Assessment of a New Prototype Hydrogel $CO_2$ Sensor; Comparison with Air Tonometry," The Journal of Clinical Monitoring and Computing 21(2):83-90, 2007.
Office action dated Jan. 9, 2009 for U.S. Appl. No. 11/828,547.
Office action dated May 14, 2009 for U.S. Appl. No. 11/828,547.
Office action dated Aug. 6, 2008 for U.S. Appl. No. 11/828,547.
Office action dated Dec. 8, 2009 for U.S. Appl. No. 11/828,547.
U.S. Appl. No. 14/053,112, filed Oct. 14, 2013.
U.S. Appl. No. 13/750,725, filed Jan. 25, 2013.
U.S. Appl. No. 13/787,171, filed Mar. 6, 2013.
U.S. Appl. No. 13/899,316, filed May 21, 2013.
U.S. Appl. No. 13/906,776, filed May 31, 2013.
U.S. Appl. No. 13/951,057, filed Jul. 25, 2013.
U.S. Appl. No. 14/557,211, filed Dec. 1, 2014.

\* cited by examiner

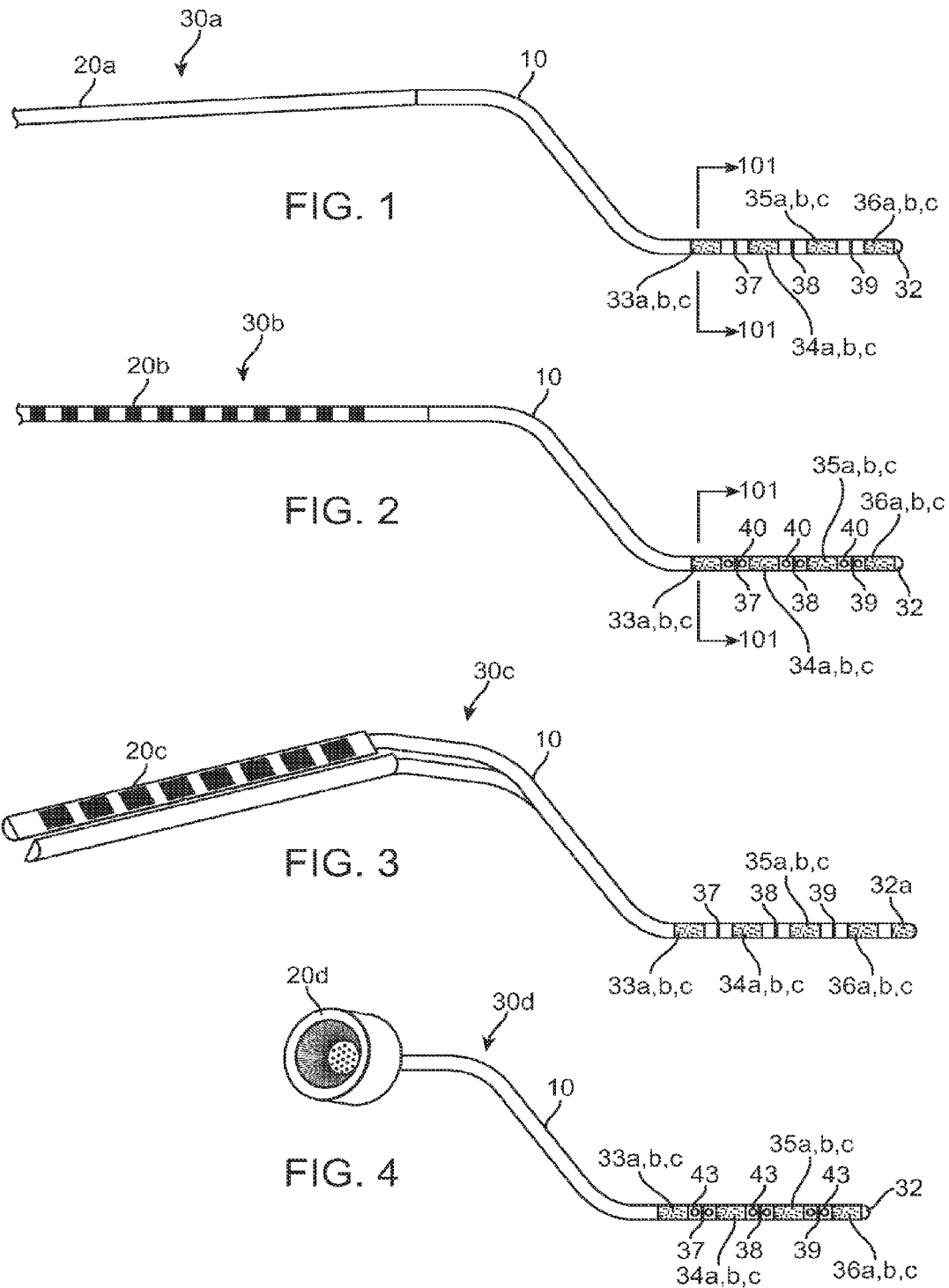

LEAD AND METHODS FOR BRAIN MONITORING AND MODULATION

CROSS-REFERENCE

The present application is a continuation of U.S. patent application Ser. No. 11/828,547, filed Jul. 26, 2007, now U.S. Pat. No. 8,321,025, which is a non-provisional of, and claims the benefit of U.S. Provisional Application No. 60/820,919, filed Jul. 31, 2006; the entire contents of each are incorporated herein by reference.

BACKGROUND OF THE INVENTION

1. Field of the Invention

This invention relates generally to medical apparatus and methods, and more specifically to leads used to electrically and/or chemically modulate and monitor tissues of the brain.

Implanting medical devices such as probes or leads within the cranium is an increasingly important approach for treatment of diseases such as Parkinson's Disease, essential tremor and dystonia. Implants may be used to treat a wide array of disorders, such as depression, epilepsy, dystonia, obsessive compulsive disorder, obesity and chronic pain. Most of these devices interact with the brain by applying current through an electrode. In addition, infusion of drugs through a chronically implanted lead has been proposed in the medical literature either as a primary treatment, or as an adjunctive treatment to electrical stimulation, in patients with Alzheimer's and Parkinson's Diseases, among others.

Current implantable probes are typically configured as small diameter cylinders or tubes, with several circumferential metal rings near the distal tip, and an electrically passive central axial lumen. The metal rings are used to provide electrical stimulation, while the central axial lumen can be used to deliver the probe over a guidewire or stylet during the implantation procedure.

In most treatment protocols, a sequence of electrical pulses is applied to one or more conducting rings on the probe. Typically monopolar or bipolar stimulation of the conducting rings is used. In monopolar stimulation, a single circumferential ring is stimulated with a charge balanced biphasic electrical pulse, with a return path for the current at a remote site, such as a battery pack or control module. In bipolar stimulation, a combination of rings are stimulated with charge balanced biphasic electrical pulses of opposite polarity. Stimulation of conducting rings produce a field of action which is more or less symmetric about the probe, with some asymmetries arising because of anisotropy in the electrical properties of the adjacent neural or brain tissue.

A symmetrical electrical field about the probe axis is not always desirable. For example, when the probe is not implanted at the center of the modulation target or when the brain target is asymmetric or irregular in shape. Additionally, there are often neuronal domains near the targeted zone, which should not be modulated. Modulating non-target zones can lead to undesirable side effects, including somatic sensation, involuntary movement and impaired vision, among others.

It is desirable to not only modulate brain activity, but also to monitor it along with physiological and pathophysiological states. Monitoring obtains information on neuronal activity near the stimulation sites, including field potentials and extracellularly recorded action potentials. Such potentials may be observed on an ongoing basis, in the course of electrical stimulation for treatment, and in the course of special stimulation and response experiments designed to assess an individual's brain and the brain to electrode interface. Information obtained from monitoring at intervals may be used to control and adjust treatment on an ongoing, day-to-day basis by a patient, or in follow up visits to a health professional. Information obtained from monitoring may also be used to dynamically adjust the treatment by an automated control system or control algorithm, and by updating the parameters of a controller.

Monitoring at intervals can be used to track changes in the brain response to stimulation as a function of stimulus magnitude. Clinical decisions can be based upon estimated parameters, such as the threshold stimulus level which barely generates a response, and the stimulus level which just saturates the observed response. The shape of the stimulus response function, for example whether it is concave up, concave down, or linear, may also inform adjustments to treatment. The dynamic range from threshold to saturation measured near the stimulation site may directly correspond to the dynamic range of clinical effect, or it may be correlated with it. In either case, the locally measured dynamic range gives information which can accelerate the initial fitting and guide ongoing adjustments in treatment protocol. Brain plasticity in response to treatment may be tracked by changes in the dynamic range.

Consider the application of monitoring at intervals to the treatment of Parkinson's disease. It is well known that the beneficial effects of electrical stimulation to Parkinson's patients do not appear for several minutes or hours after the stimulation protocol is initiated. If the protocol is discontinued during sleep and resumed at waking, the beneficial effects of treatment may not appear again for many hours. Monitoring at intervals offers the opportunity to track changes in the response to stimulation, so that stimulation can be applied during one protocol in order to bring about the beneficial effects, and under another more conservative protocol in order to just maintain the beneficial effects. Such a strategy would conserve battery power, and could also reduce side effects.

By monitoring from moment to moment, a modulatory treatment can be dynamically synchronized with natural brain rhythms upon an observed pathological or normal physiological state, or controlled by an automatic control system or control algorithm.

Most procedures currently performed monitor patient motions, behaviors, or brain activity at a site remote from the site of an electrically stimulating probe, and this information is used to adjust brain stimulation parameters. Parameters are adjusted on a short time scale, to generate a desired effect and minimize side effects, and on a longer time scale, to account for brain plasticity. Brain plasticity is due to an adaptive response by the brain to an intervention and it is well known that ongoing responses by the brain to an intervention such as modulating therapy often differ from the initial response. Useful information may also be obtained by monitoring electrical potentials near the site of electrical stimulation and therefore it would be desirable to monitor brain activity at the locus of electrical stimulation. Monitoring allows the course of the disease and healing processes to be evaluated along with the prognosis for various treatment options.

For these reasons as well as others, it would be desirable to provide improved probes for modulating and monitoring tissues such as the brain. It would be particularly desirable to provide an efficient design for generating a directed electrical field that may be steered towards the intended target, and/or away from other brain areas. It is also desirable to provide a probe with an efficient number and size of electrodes as well as connector leads, that integrates both electrical recording and stimulating or modulating capabilities, where the information from recordings is obtained close to the treatment site and can be used to define the stimulating protocol. The protocol can then be adapted either statically or dynamically and as the disease state changes, the therapy can also be adjusted. Recording and monitoring of brain electrical activity is also used to determine when the stimulation protocol is applied or whether it should be reserved for times when it is more effective, thereby helping to conserve power.

2. Description of the Background Art

Prior patents and publications describing brain modulating probes and methods include: U.S. Publication Nos. 2006/0047325; 2006/0004422; 2005/0015130; 2004/0039434 and U.S. Pat. Nos. 7,051,419; 7,047,082; 7,006,872; 6,094,598; 6,038,480; 6,011,996; 5,843,148; and 5,716,377.

SUMMARY OF THE INVENTION

The invention generally provides an implantable probe or lead capable of modulating or stimulating tissue and measuring and recording local tissue responses as a result of the modulation. The terms "modulating" and "stimulating" are used interchangeably in order to refer to providing a stimulus that incites or suppresses activity in the tissue. The terms "probe" and "lead" are also used interchangeably in order to refer to any device that may be used to modulate the tissue and/or measure and record local tissue responses. Modulation of the tissue may include electrical and/or chemical stimulation of the tissue, as well as suppression of tissue activity. Measuring and recording tissue responses often entails measuring local tissue potentials in response to the stimulation but could also include measuring and recording endogenous tissue potentials as well as chemical activity in the tissue. Often, the probe is used in tissues of the brain, typically being implanted into deep brain structures, or into the cerebrum or cerebellum.

The invention also provides methods where therapeutic modulation may be directed within tissues such as neural structures with improved effectiveness and minimal undesirable side effects. The present invention also includes methods to electrically and/or chemically monitor tissue activity so that the therapeutic intervention may be modified to improve its effectiveness, or to conserve limited resources such as reagents or electrical charge.

The probe possesses electrodes for stimulating tissue such as the brain, and/or for recording tissue activity by measuring local tissue potentials. The stimulating electrodes are arranged so that they can be activated individually, or in combination. They may alternatively be activated in simultaneous or sequential coordination in order to shape the volume of stimulated brain tissue and regulate the magnitude and timing of activity in a stimulated brain. The probe often has a plurality annular shaped stimulating electrodes disposed axially along the probe. For the most efficient use of the probe, each annular shaped electrode has three independent stimulation sites disposed thereon, although a greater number of stimulation sites per annular region may be employed. By "independent stimulation sites," it is meant that the electrode is separable into three isolated regions, typically disposed in 120° arcs of the annular electrode, where each region may be independently energized from an external or other energy source.

In a first aspect of the invention, an apparatus for stimulating and monitoring brain tissue comprises an elongate member having proximal and distal ends, and a plurality of annular stimulating electrodes axially arranged along the elongate member, disposed near the distal end, but may also be disposed at other axial positions. Portions of the elongate member may be flexible, often near the proximal end and portions may also be rigid near the distal end. The annular stimulating electrodes are adapted to pass current into tissue and at least one of the annular stimulating electrodes has at least three independent stimulation regions or points. The apparatus will usually but not necessarily further comprise a plurality of measuring or recording electrodes disposed adjacent to the stimulating electrodes and some of the recording electrodes may be arranged between annular stimulating electrodes and the recording electrodes are adapted to measure local tissue potentials. The recording electrodes may be circumferentially disposed about the elongate member and sometimes have a circular shaped surface. There may also be a surface for recording and/or stimulating at or near the tip of the apparatus. The apparatus will usually include a plurality of conductors which are coupled with at least some of the annular stimulating and annular recording electrodes, and an optional multiple contact connecting terminal may be disposed near the proximal end of the elongate member and that is coupled with the conductors. The apparatus may have one conductor per stimulating and/or one conductor per recording region. Often the apparatus also has a lumen that is axially disposed between the proximal and distal ends and sometimes the lumen is adapted to receive a guidewire or stylet.

Often the tissue being treated is brain tissue, although other tissues may also be treated by the method and system of the present invention. Additionally, the apparatus often includes a lumen axially disposed along or within the elongate member. In some cases the lumen is adapted to receive a guidewire or stylet, which passes through the lumen from a port near the distal end of the elongate member. In other cases, one or more ports in communication with the lumen are disposed near the distal end of the elongate member and are adapted to deliver a therapeutic agent or other substance to the tissue and/or to receive a chemical substance from the tissue. In some cases, the ports are disposed between the annular stimulating electrodes and in other cases, at least one of the ports is disposed at the distal end of the elongate member. In some embodiments, the ports may comprise a gating member adapted to permit selective enablement of the ports. The gating member may be a semi-permeable membrane and may be chemically controlled such as when the gating member is a chemically reactive hydrogel.

In some embodiments, an additional stimulating electrode may be disposed in the lumen, and often this additional electrode is a wire. Therapeutic agents may also be delivered through the lumen. In other embodiments, an additional stimulating electrode may be placed at the distal end of the elongate member and this electrode is also capable of passing current into the tissue. A therapeutic agent may also be used with this or other embodiments described herein. Often, the conductors are helically wound along the elongate member. A first group of conductors may be coupled with the stimulating electrodes, and a second group of conductors may be coupled with the recording electrodes. The first group of conductors may be wound in a helix having a first pitch, and the second group of conductors may be wound in a helix having a second pitch. In some cases, the first pitch is different than the second pitch. Conductors are often comprised of stainless steel, MP35N or tungsten because of their biocompatibility and compatibility with MRI imaging systems, although other materials such as platinum-iridium alloy are possible. Typically, the plurality of annular stimulating electrodes, as well as the recording electrodes may also be compatible with magnetic resonance imaging (MRI). An object is compatible with MRI if it does not significantly distort image quality, cause tissue damage with heating and does not move in the presence of a magnetic field.

In a second aspect of the present invention, a method of treating tissue comprises implanting a probe in the tissue. The probe may be compatible with magnetic resonance imaging and usually has a plurality of annular stimulating electrodes as well as a plurality of recording electrodes. At least one of the annular stimulating electrodes has at least three independent stimulation points or regions on it. The tissue can then be stimulated with a therapeutic electrical current from the annular stimulating electrodes, and local tissue potentials may be measured, typically in response to the stimulation with the recording electrodes. Chemical substances from the tissue may also be collected in order to provide feedback on the effectivenss of the stimulation and this may include controlling a gating member so as to selectively open or close one or more ports disposed on the probe. The ports may also be adapted to control delivery of a therapeutic agent to and/or received a chemical substance from the tissue. The measured local tissue potentials may be analyzed to provide feedback on the effectiveness of the stimulation, and then stimulation may be adjusted in response to the feedback. Often the tissue being treated is brain tissue, and the method may further comprise stimulating the tissue with a therapeutic agent. The method may also comprise releasably coupling the probe to the tissue with an anchor.

In a third aspect of the present invention, a system for treating tissue comprises a tissue probe compatible with magnetic resonance imaging and usually having a plurality of annular stimulating electrodes as well as a plurality of recording electrodes adapted to measure local tissue potentials. At least one of the annular stimulating electrodes has at least three independent stimulation points or regions on the electrode, and the regions are adapted to pass current into tissue. The system may also include a multiple contact connector coupled with the recording and stimulating electrodes and an implantable and controllable pulse generator that is adapted to provide an electrical stimulus to the tissue probe via the multiple contact connector. Typically the tissue being treated is brain tissue, and the system often may comprise an anchoring device. The anchoring device is adapted to removably fix the tissue probe to a patient's head. The system also typically includes a patient programmer that is adapted to control the pulse generator.

These and other embodiments are described in further detail in the following description related to the appended drawing figures.

BRIEF DESCRIPTION OF THE DRAWINGS

FIG. 1 illustrates one embodiment of a tissue monitoring and modulation lead.

FIG. 2 illustrates another embodiment of a tissue monitoring and modulating lead.

FIG. 3 illustrates yet another embodiment of a tissue monitoring and modulating lead.

FIG. 4 illustrates still another embodiment of a tissue monitoring and modulating lead.

DETAILED DESCRIPTION OF THE INVENTION

Figure 5:
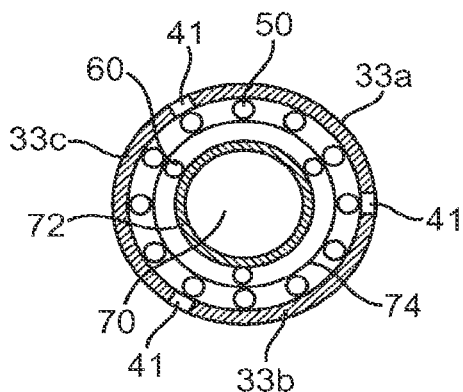
FIG. 5 illustrates a cross-section of a tissue monitoring and modulation lead.

In the drawings like numerals describe substantially similar components. Probes often have annular electrodes on their distal ends. An electrode divided into two stimulation sites is capable of orienting a dipole along one axis. When the annular electrode is divided into three stimulation sites, a dipole may be generated along any direction in a plane. Three stimulation sites per annular electrode is therefore advantageous as being the minimum number of stimulation sites per electrode required to orient a dipole along any direction in a plane. Using the minimum number of stimulation sites is also advantageous because it minimizes the number of conductors which must pass through the probe and permits maximum current density through any recording site to modulate the brain tissue.

Figure 14:
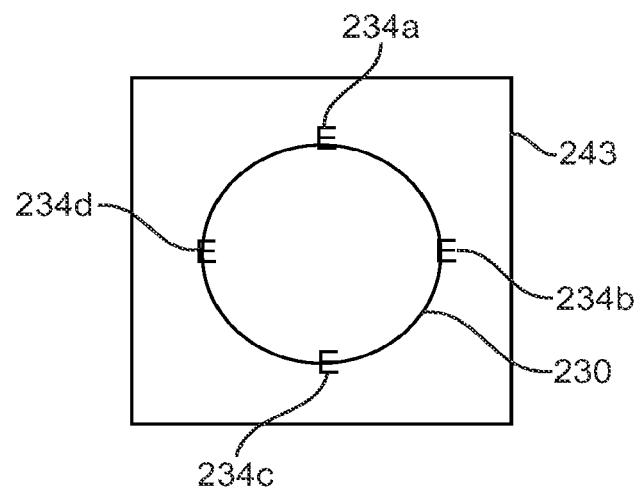
FIG. 14 illustrates a model of the magnitude of a dipole generated by four stimulation sites separated by 90°.

When current density is limited by brain tissue tolerance, a broken ring of stimulation sites can deliver a greater stimulus in some directions than others. For example, consider four stimulation sites arranged as a broken ring around a cylindrical probe, with two sites aligned with a transverse axis (X), and the other two sites aligned with an orthogonal transverse axis (Y). This configuration may generate an electrical dipole of any orientation within the plane of the stimulation sites by linear summation of two dipoles resulting from passing electrical current between opposite pairs of stimulating sites. To generate a dipole of magnitude (m) and orientation θ relative to axis (X), a current of magnitude (m/d) cos θ is passed through stimulating sites aligned with (X), and magnitude (m/d) sin θ is passed through the stimulating sites aligned with (V), and where d is the distance from the origin. As θ changes, the locus of the dipole magnitude traces a circle. It may be desired to limit the current density at any single electrode to be less than some maximum value, so that heat or other undesired side effects of stimulation may be limited. With such a constraint, the maximum dipole that may be generated by a broken ring of four stimulation sites as a function of the angle θ traces a square 243, as seen in FIG. 14. The largest dipole magnitudes are for orientations midway between the axes (X) and (Y), at the corners of the square, because both pairs of stimulation sites carry the maximum permitted current. The smallest dipole magnitudes are for orientations along the axes (X) and (Y), because only one pair of stimulation sites carries nonzero current.

Compare the above scenario to an embodiment with three stimulation sites arranged in a broken ring or annulus about a cylindrical probe. If the axial extent of the electrode ring and maximum current density are the same as in the previous example, the maximum magnitude of the current through any electrode is ⅓ greater. When the maximum current is passed through one electrode, the return current is divided in various proportions between the other two electrodes. The maximum dipole that can be generated by a ring of three electrodes as a function of θ traces a hexagon 246, similar to that illustrated in FIG. 15. For most orientations of the stimulating field, the magnitude of the maximum dipole generated by a broken ring of three stimulation sites is greater than the dipole generated by a broken ring of four stimulation sites as seen by the square 243 from FIG. 14 superimposed in FIG. 15.

Figure 15:
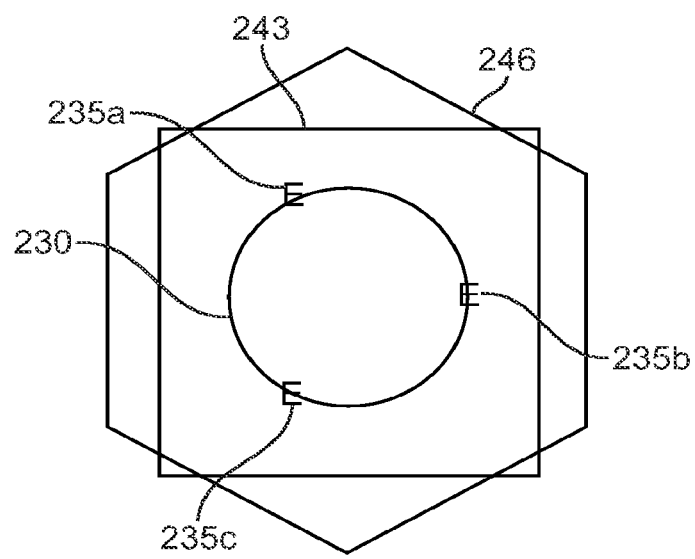
FIG. 15 illustrates a model of the magnitude of a dipole generated by three stimulation sites separated by 120° as compared with the model in FIG. 14.

FIGS. 14 and 15 illustrate a simplified model which clarifies the advantages of using a prime number of stimulation sites such as three. There are three stimulation sites on a broken ring in the preferred embodiment of FIG. 1. FIG. 14 illustrates the case of four electric monopoles 234*a*, 234*b*, 234*c* and 234*d* arranged at points around a circle 230. Monopoles 234*a* and 234*c* are equally and oppositely charged, and generate a dipole, as do monopoles 234*b* and 234*d*. The radial position of points on the square 234 represent the maximum net dipole that can be created by the sum of the two dipoles 234*a*, 234*c* and 234*b*, 234*d*, subject to the constraint that the maximum charge on a monopole is of magnitude one. The sum of the charge of the four monopoles is zero.

FIG. 15 illustrates the case of three electric monopoles 235*a*, 235*b* and 235*c* arranged at points around a circle 230. The maximum net dipole square 243 of FIG. 15 is superimposed here for reference. Three electric monopoles generate an oriented dipole more efficiently, as diagrammed by maximum net dipole hexagon. Two dipoles are generated by one monopole of one polarity, and two of the opposite or zero charge. The sum of the charge of all three monopoles is zero. The radial position of points on the hexagon 246 represent the maximum net dipole that can be created by the sum of the two dipoles, subject to the constraint that the maximum charge on any monopole cannot exceed the magnitude 1.2. The larger maximum charge constraint is used here because the surface area of each stimulation site of a fixed axial length is greater if each portion occupies ⅓ of the circumference, than if each portion occupies ¼ of the circumference. The sides of the hexagon nearest the electrodes 235*a*, 235*b*, 235*c* are generated in the situation where the constraining electrodes has positive polarity, and the sides of the hexagon opposite these are generated in the situation when the constraining electrode has negative polarity. It can be seen that the radial position of the hexagon 246 is farther from the origin than the square 243 at most directions from the origin. For a fixed axial extent of the broken ring, three stimulation sites can deliver a larger effective stimulus compared to four stimulations sites. Alternatively, for a fixed effective stimulus, the axial length of a broken ring of 3 stimulation sites can be shorter than for a broken ring of 4 stimulation sites. The preferred embodiment of the invention has the advantage over other probes of supporting better steerability of the electric current for the situation in which the maximum current density is constrained. This description of the invention does not preclude using a stimulation protocol in which stimulation sites on different broken rings are stimulated simultaneously or in coordination.

It will be apparent to those skilled in the art that a stimulating probe with a broken ring of 6 stimulation sites (or any other multiple of 3) can be used in a manner so as to obtain the advantages of this invention. This may be accomplished by controlling the ring of six stimulation sites as three stimulation sites, each comprised of a pair of adjacent stimulation sites.

Therefore, at any axial position, the number of stimulation sites is a prime number. A prime number yields more combinatorial possibilities for simultaneously using all electrode surfaces to achieve different stimulation orientations. Using all electrode surfaces keeps current density as low as possible. In a preferred embodiment, the number of stimulation sites is 3. In another embodiment, the number of stimulation sites is 5. Configurations with 2, 5 or 7 stimulation sites could achieve the current density advantages which this invention seeks to achieve also, although to a lesser degree.

Referring now to FIG. 1, a tissue modulating and monitoring probe is illustrated. FIG. 1 shows a preferred embodiment of the probe. It is a cylindrical probe, with a flexible probe body 10 and an optional multiple contact connecting terminal 20*a*. Additional details on multiple contact connecting terminals are disclosed in U.S. Provisional Application No. 60/820,914 the entire contents of which are incorporated herein by reference. Other connectors may be used and are well known in the art. At the distal end of the probe 30*a* there are one or more broken annular rings of stimulating sites. The stimulating sites may be aligned with matching angular position on all rings, or may be offset to different angular positions on different rings. There are also one or more circumferential electrode bands suitable for recording local field potentials, and a recording electrode at or near the most distal point. In this preferred embodiment, the maximum diameter of the multiple contact terminal 20*a* is the same as the diameter of the flexible probe body 10.

In this embodiment, at four axial positions, three stimulation sites 33*a*, 33*b*, 33*c*, 34*a*, 34*b*, 34*c*, 35*a*, 35*h*, 35*c*, 36*a*, 36*b*, 36*c* are arranged as broken rings, for a total of 12 stimulation sites. These are better seen in the cross-sectional views of FIGS. 5-12. Also in this embodiment are three recording bands 37, 38, 39 arranged in the gaps between the broken rings. The size of the recording sites is suitable for recording local field potentials, with an exposed area ranging from about 0.0005 mm$^2$ to about 0.5 mm$^2$ but the area could be up to about 0.8 mm$^2$. Some embodiments have smaller recording sites that improve extracellularly recordings of action potentials. Such recording sites range in exposed area from about $1.9 \cdot 10^{-5}$ mm$^2$ to about 0.002 mm$^2$, but they could be as large as about 0.1 mm$^2$. The form of the recording sites could be the bare end of an insulated wire, a thin film, a metal pad, or an insulated region with a portion of the insulation removed to expose an electrical conductor within the wall of the device. Alternative embodiments may have no recording rings, or may have more recording rings. Additional recording rings or point electrodes may be located along the probe body 10 or at the probe tip 32. The embodiment does not restrict the alignment of the recording electrodes (bands and/or points) with respect to the stimulation sites.

There must be a nonconductive gap of at least 100 μm between stimulating and recording surfaces, and between recording surfaces, to reduce shunting and improve the isolation of the recorded signals, it is desirable that electrical signals traversing through the probe do not interfere with each other. It is especially desirable that the high level electrical stimulation signals not interfere with the low level recording signals. Therefore, it is preferable that the conductors carrying recording signals lay in an inner helix, while conductors carrying stimulation signals lay in an outer helix. The pitch of the two helices may be the same or may be different, so that no pair of stimulation and recording conductors traverse adjacent paths for an appreciable distance. This minimizes capacitive coupling between any stimulating conductors and any recording conductors. In other embodiments, a conductive coating may be applied to the outside of the helix of recording conductors. This can be grounded to decrease electromagnetic interference between the two types of conductors. In yet another embodiment, a metal foil, which may be grounded, is wrapped between the inner and outer wire helices.

There must be a nonconductive gap of at least 100 .mu.m between stimulating and recording surfaces, and between recording surfaces, to reduce shunting and improve the isolation of the recorded signals. It is desirable that electrical signals traversing through the probe do not interfere with each other. It is especially desirable that the high level electrical stimulation signals not interfere with the low level recording signals. Therefore, it is preferable that the conductors carrying recording signals lay in an inner helix, while conductors carrying stimulation signals lay in an outer helix. The pitch of the two helices may be the same or may be different, so that no pair of stimulation and recording conductors traverse adjacent paths for an appreciable distance. This minimizes capacitive coupling between any stimulating conductors and any recording conductors. In other embodiments, a conductive coating may be applied to the outside of the helix of recording conductors. This can be grounded to decrease electromagnetic interference between the two types of conductors. In yet another embodiment, a metal foil, which may be grounded, is wrapped between the inner and outer wire helices.

In other embodiments, the conductors carrying recorded signals lay between conductors carrying electrical stimulation signals. This embodiment has the advantage that the conductors lay in a single lamina and can be more compact and more flexible, although in some instances this embodiment may have the disadvantage that when stimulating current modulates a stimulating conductor, the stimulation signal may couple into adjacent recording conductors. Note that not all of the stimulus conductors are required to carry a current at any instant. In many uses of the probe, some of the recording conductors will therefore be well separated from active stimulating conductors at any instant. In another embodiment, the stimulating wires and recording wires course as adjacent groups of conductors in a helix.

The wires should be mechanically strong and electrically conductive. Suitable materials include alloy MP35N (cobalt chrome alloy), stainless steel, and tungsten or tungsten alloy wire which has been gold plated to facilitate continuity with the stimulation sites and to the extra-cranial connector. It is important that the material be minimally magnetic to maximize MRI compatibility.

Stimulation sites are made of a relatively inert material which maximizes safe charge transfer, such as platinum, iridium or an alloy of platinum and iridium. The body of the probe is coated by a biocompatible polymer, such as silicone rubber or polyurethane, which supports bending with a short radius of curvature where the probe exits the cranium.

FIG. 2 illustrates an alternative embodiment of the probe 30b. Probe 30b is similar to the probe 30a of FIG. 1 except that it adds ports 40 which may permit chemical substances to enter or leave the probe lumen. The ports 40 may be covered by a semi-permeable membrane. Alternatively a chemically controlled gating mechanism, such as a chemically reactive hydrogel, may be placed near the ports. Such a hydrogel can swell or contract depending upon the chemical composition of the adjacent medium. The gating mechanism may operate based on bulk swelling and occlusion of the port, or the hydrogel may be formed with a mechanical accessory structure. An example of such is structure includes a bimorph beam as described by R. Bashir, J. Z. Hilt, O. Elibol, A. Gupta, and N. A. Peppas in "Micromechanical Cantilever as an Ultrasensitve pH Microsensor," published in Applied Physics Letters, 81(16):3091-3093, 2002. Another example includes a surface covering fenestrated with microports as disclosed by A. Baldi, M. Lei, Y. Gu, R. A. Siegel and B. Ziaie in an article entitled "A Microstructured Silicon Membrane with Entrapped Hydrogels for Environmentally Sensitive Fluid Gating," published in Sensor and Actuators B, 114(1):9-18, 2006, or another example includes a pad which displaces elements suited to forming an occlusive seal as described by A. Baldi, Y. Gu, P. E. Loftness, R. A. Siegel and B. Ziaie in "A Hydrogel-Actuated Environmentally Sensitive Microvalve for Active Flow Control," published in the Journal of Microelectromechanical Systems, 12(5):613-621, 2003. The entire contents of these references are incorporated herein by reference.

Since the hydrogels may be formulated such that their volume has different chemical dependencies, different hydrogels may be associated with ports at different pre-determined positions on the lead, so that drugs may be delivered selectively to pre-determined positions on the probe. Likewise, samples of the extra-cellular space or cerebral spinal fluid (CSF) may be obtained from pre-determined positions on the probe. Examples of chemical gating mechanisms that are controlled directly by pH include those described previously in "Micromechanical Cantilever as an Ultrasensitve pH Microsensor. Gating mechanisms controlled by the presence of carbon dioxide via a relationship to pH include those described by R. Steege, H. Sebastiaan, W. Olthuis, P. Bergveld, A. Berg, and J. Kolkman in "Assessment of a New Prototype Hydrogel CO2 Sensor; Comparison with Air Tonometry," as published in The Journal of Clinical Monitoring and Computing 21(2):83-90, 2007. Other examples of gating mechanisms controlled by the presence of glucose are disclosed by Theeuwes et al. in U.S. Pat. No. 6,997,922. The entire contents of the above listed references are incorporated herein by reference.

FIG. 3 illustrates an alternative embodiment of probe 30c in which the probe tip 32a is electrically conductive, serving as an additional stimulation site. This could serve as a conventional stimulation site, supporting monopolar and bipolar stimulation. In conjunction with a distal ring of stimulation sites 36a-c it forms a group of stimulation sites centered on the vertices of a tetrahedron, supporting steering of the current near the tip in three dimensions. The embodiment of FIG. 3 also has an additional recording electrode 42 between stimulating electrodes 36a-36c and distal stimulating electrode 32a. Also, multiple contact connecting terminal 20c has a plurality of electrical contacts axially spaced along two hemi-cylindrical or D-shaped connectors, as further disclosed in U.S. Provisional Patent Application No. 60/820,914 the entire contents of which are incorporated herein by reference.

FIG. 4 illustrates an alternative embodiment of the probe, 30d, demonstrating that the multiple contact terminal 20d need not have the same diameter as the probe body 10. Here, contact terminal 20d is a larger diameter cylindrical shaped plug with receptacles for coupling the probe 30d with the rest of the monitoring and modulation system. This embodiment illustrates that the surface of recording electrodes need not be circular, but may be configured as recording points 43. Alternative embodiments may include multiple recording sites, some configured as rings, and other configured as points. In other embodiments the recording electrodes may take other shapes, including squares, rectangles or irregular shapes. In yet another alternative embodiment, the multiple contact terminal may allow for a lumen or conduit for the passage fluid within the probe. Fluid may pass in one or more lumens, and may flow into or out of the brain, or both.

FIG. 5 illustrates an axial cross-sectional view of a preferred embodiment, at section line 101 in FIG. 1. In the preferred embodiment the central lumen 70 is surrounded by a tube 72 made of a biocompatible polymer, such as polyurethane, silicone rubber or polyamide. In alternative embodiments the lumen is a polymer coating, and the insulated recording conductors 60 may reside in the inner lumen. Recording conductors 60 are wound in a helix from the recording sites to their termination at the contact terminal 20. Likewise, the stimulating conductors 50 are wound in a helix from the stimulation sites to their termination at the contact terminal 20. In a preferred embodiment, the stimulating conductors 50 have larger size than the recording conductors 60 because resistive losses are a greater concern for the stimulating conductors 50, but all conductors may be of the same or similar dimension in alternative embodiments. In a preferred embodiment, the pitches of the recording wire helix and the stimulating wire helix are different, to decrease the average capacitive coupling between the wires. In alternative embodiments the helices could have the same pitch. The two helices may have the same or opposite orientation (one clockwise, the other counterclockwise). Conductors 50, 60 are embedded in a flexible polymer, and are insulated in the preferred embodiment, but could or could not rely on the surrounding polymer for insulation in an alternative embodiment. In the preferred embodiment, a layer of electrically conductive material 74 is interposed between the recording and stimulating conductors, which may be attached to a low impedance electrical reference. Alternative embodiments may use layer 74 or the central lining of the central lumen 72 as an internal stimulating electrode. Alternative embodiments may omit this layer 74 to simplify manufacturing. Stimulation sites 33a-c lay on the surface of the probe, with gaps of nonconductive material 41 between them. The stimulation sites 33a-c may be of the form of sections of a tube adhered to the probe, and welded or riveted to the conductors 50, or may be fabricated with thin film technology. Examples of thin film technology that could be used to fabricate the probe are described, for example, in U.S. Pat. Nos. 7,051,419 and 7,047,082 the entire contents of which are incorporated herein by reference. The conductors 50, 60 in FIG. 5 are shown as having a circular profile to suggest transversely cut round wires, but alternative forms could use shaped wires such as those having a square, rectangular or elliptical cross-section, or thin film technologies may be used for the conductors. FIG. 5 shows 12 stimulating conductors 50 and 3 recording conductors 60 corresponding to the preferred embodiment, but alternative embodiments could have more or fewer conductors to support various numbers of electrodes.

Figure 6:
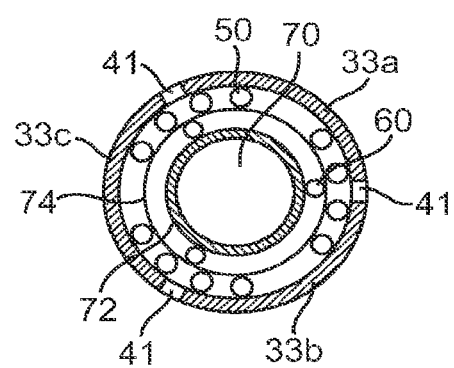
FIG. 6 shows a cross-section of an alternative embodiment of a monitoring and modulation lead.

FIG. 6 illustrates an alternative embodiment, in which the stimulating conductors 50 are arranged in groups rather than uniformly spaced around the circumference of the probe. Three groups of four are illustrated, but alternatively the conductors could be arranged in 4 groups of three. Such embodiments could allow for ports communicating between the central lumen 70 and the outside of the probe, or for improved flexibility of the probe in conjunction with reduced wall thickness between groups of conductors.

Figure 7:
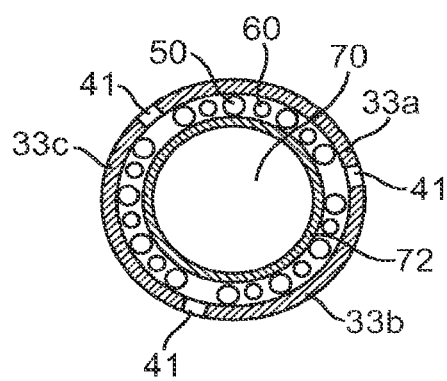
FIG. 7 shows a cross-section of yet another embodiment of a monitoring and modulation lead.

FIG. 7 illustrates an axial cross-sectional view of an alternative embodiment, at section line 101 in FIG. 1. In this embodiment, the stimulating and recording conductors are in the same annular space of the probe, unlike prior embodiments where the conductors are separated. Because this embodiment places both conductors in the same annular space, the central lumen 70 may be larger. In a preferred embodiment the stimulating conductors 50 and recording conductors 60 alternate around the helix, but in alternative embodiments the stimulating conductors and recording conductors could course as separate groups. In alternative embodiments, there may be additional conductors between the stimulating 50 and recording 60 conductors, which may be connected to the point of electrical neutrality. In alternative embodiments, the tube 72 may be coated with an electrically conductive material, which may be connected to the point of electrical neutrality.

Figure 8:
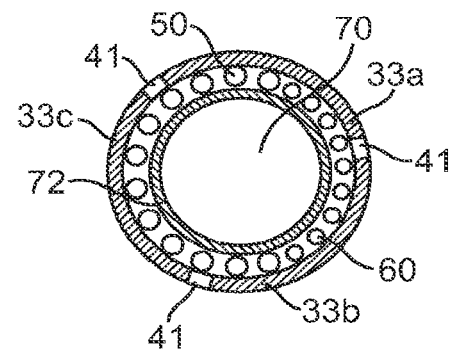
FIG. 8 shows a cross-section of still another embodiment of a monitoring and modulation lead.

FIG. 8 illustrates an alternative embodiment wherein the recording conductors 60 and stimulating conductors 50 are separated into groups. This embodiment has the advantage of reduced opportunities for undesirable capacitive coupling between stimulating and recording conductors compared to the embodiment illustrated in FIG. 7, but increases the opportunities for undesirable capacitive coupling between separate recording conductors.

Figure 9:
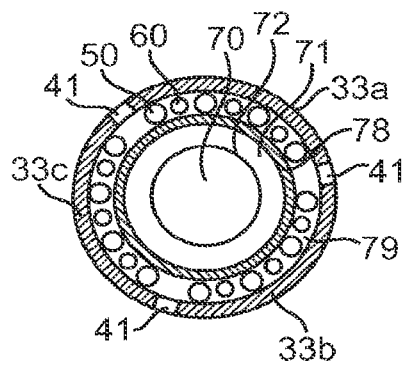
FIG. 9 shows another cross-section of another embodiment of a monitoring and modulation lead.

FIG. 9 illustrates an embodiment with dual lumens, central 70 and annular 71, to permit delivery or sampling of a fluid (gas or liquid) substance or drug, or sampling of a liquid or volatile substance. The lumens may communicate with ports, shown as 40 in FIGS. 2 and 13A-13C, and such communication may be electrically or chemically gated. The distal ends of the lumens may be closed, permeable, selectively permeable, or open, to release the lumen contents or some fraction or portion of the lumen contents. The distal ends of the two lumens may communicate with each other, so that one delivers a liquid containing a drug such a levodopa, or a gaseous medium with bioactive effects such as carbon monoxide or nitrous oxide, and another lumen retrieves the medium, after an opportunity to exchange substance or substances with the medium near ports 40 or other openings in the probe. Other therapeutic agents that may be delivered are well known in the art, such as those disclosed in U.S. Pat. Nos. 6,094,598 and 6,227,203 both of which, the entire contents are incorporated herein by reference and often, extracellular fluid such as cerebral spinal fluid (CSF) is sampled. In this embodiment, conductors for electrical stimulating and recording course together within an additional annulus 79 created by an additional wall 78 in the probe.

Figure 10:
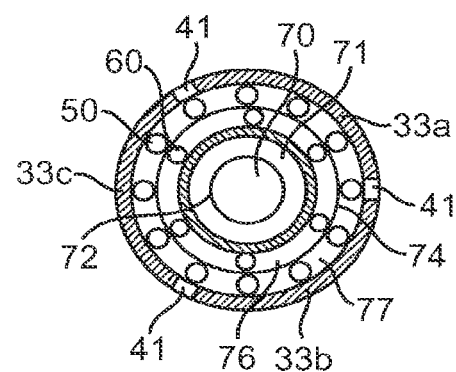
FIG. 10 shows yet another cross-section of an embodiment of a monitoring and modulation lead.

FIG. 10 illustrates an arrangement similar to that in FIG. 9, except that the conductors for stimulating and recording course through two separate annular rings 76 and 77, both concentric to the inner two lumens 70 and 71. In other embodiments, there may be more than two lumens, and the lumens need not be concentric.

Figure 11:
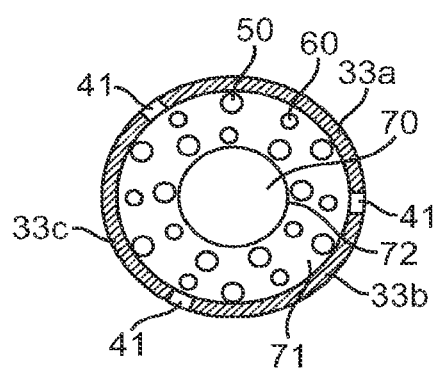
FIG. 11 shows still another cross-section of another embodiment of a monitoring and modulation lead.

FIG. 11 illustrates an arrangement similar to that in FIG. 9, except that there is a single lumen 72. Additionally, conductors 50 and 60 are randomly oriented and therefore may allow the probe to be more easily fabricated as opposed to a probe with conductors in a defined pattern.

Figure 12:
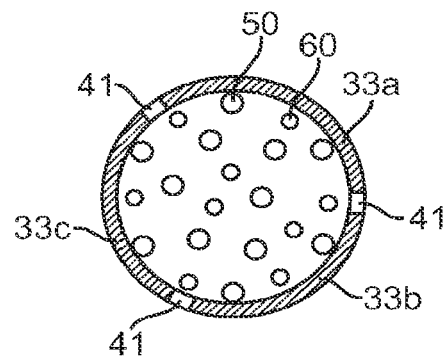
FIG. 12 shows another cross-section of another embodiment of a monitoring and modulation lead.

FIG. 12 illustrates an arrangement with no lumen for either a guide wire, or for supporting mass transfer. The conductors course together through the center of the probe.

Figure 13A:
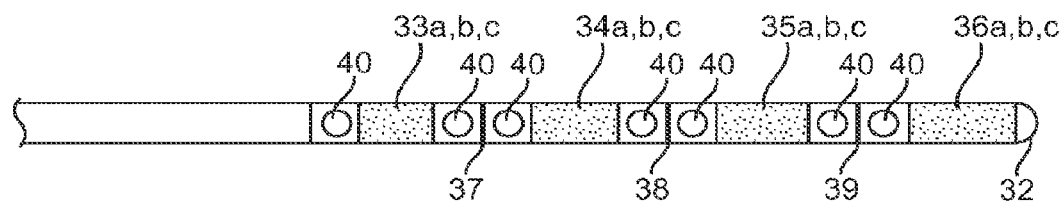
FIGS. 13A-13C highlight the recording and stimulating regions of an exemplary embodiment of a monitoring and modulation lead.
Figure 13B:
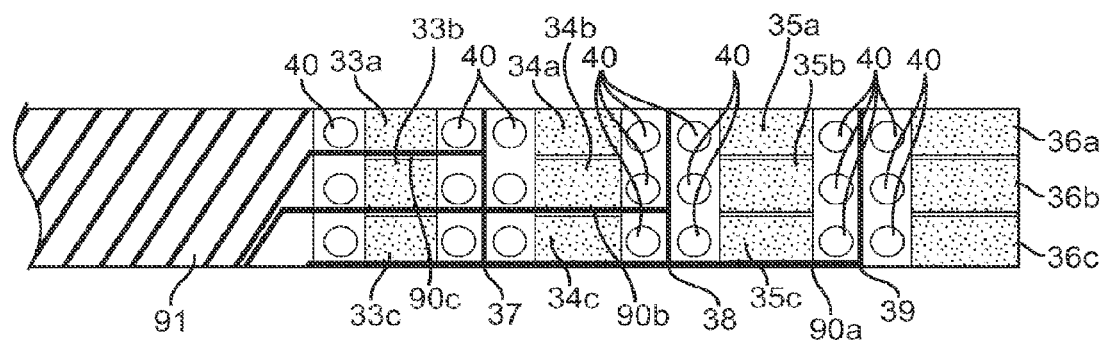
Figure 13C:
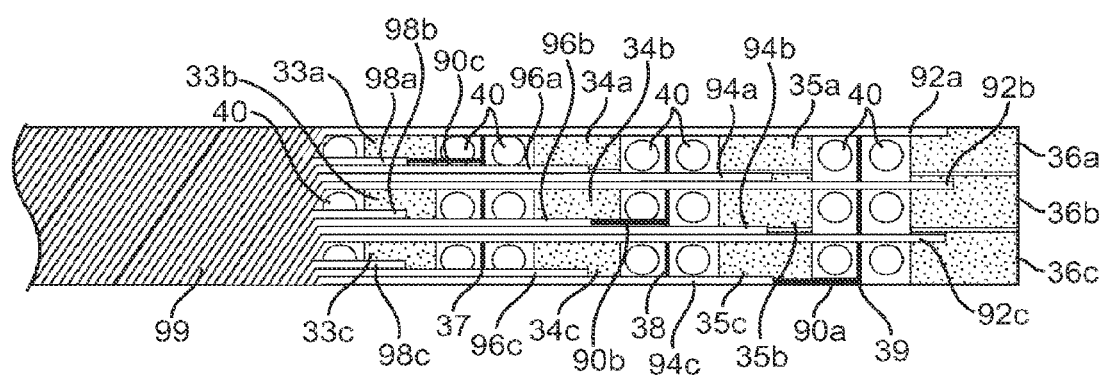

FIGS. 13A-13C illustrate an arrangement for the stimulating and recording conductors, similar to the embodiments illustrated in FIG. 2. FIG. 13A shows a probe having four regions of stimulating electrodes 36a-36c, 35a-35c, 34a-34c and 33a-33c, with each region having three independent stimulation sites. Additionally, the probe in FIG. 13A has recording electrodes 37, 38 and 39 as well as ports 40. The probe of FIG. 13A is shown in FIGS. 13B-13C with the circumference of the probe unwrapped, such that the upper edge and the lower edge of the conductors are actually continuous with each other. In the region of the probe tip, the conductors course in the axial direction, and turn to form helical windings along the probe body. FIG. 13B shows the recording electrode conductors 90a, 90b and 90c coursing in the axial direction near the probe tip and then turning to form helical windings along the probe body. FIG. 13C illustrates a similar pattern for stimulating electrode conductors 92a, 92b, 92c, 94a, 94b, 94c, 96a, 96b, 96c and 98a, 98b, 98c.

Figure 16:
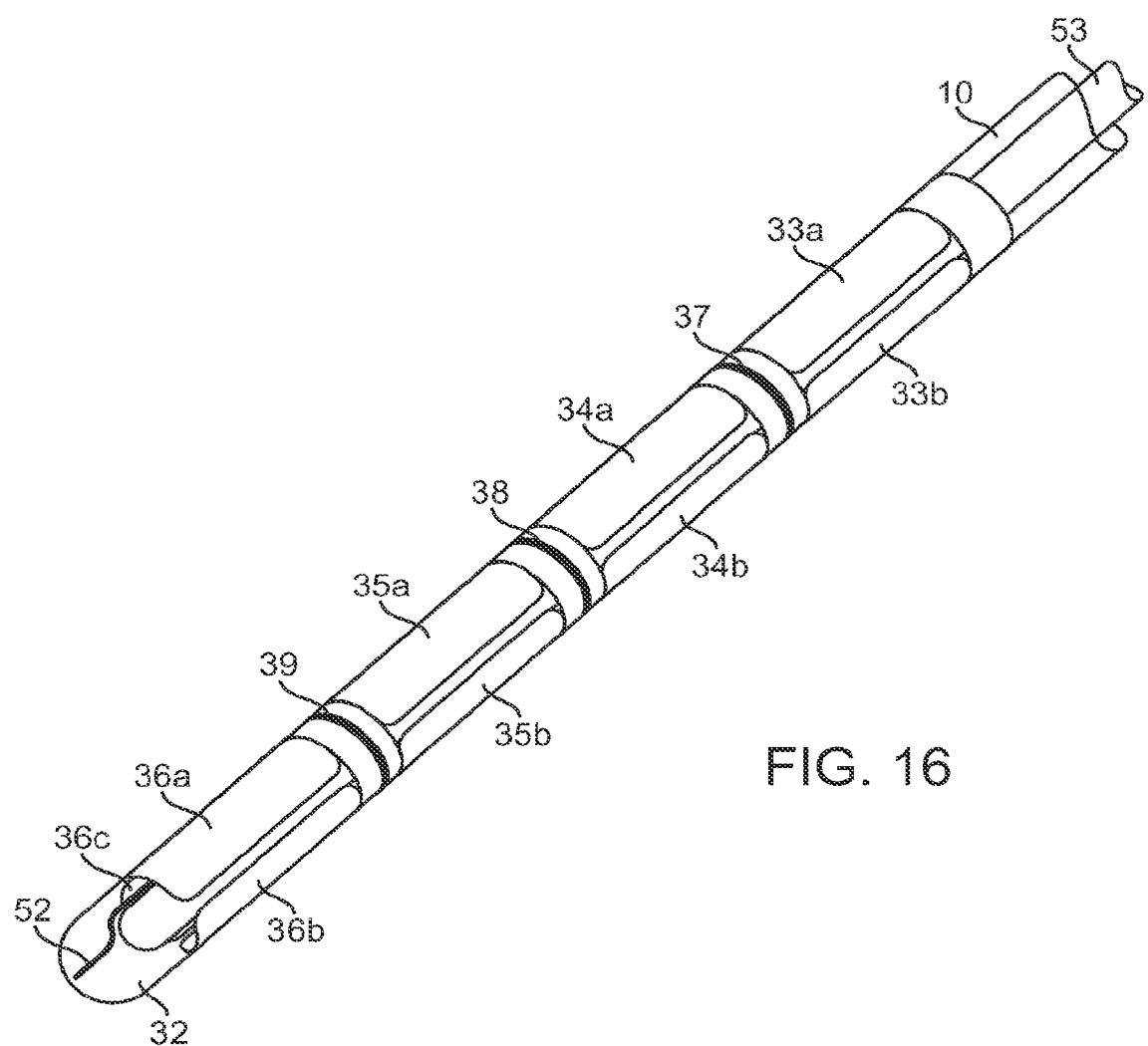
FIG. 16 shows a perspective view of an embodiment of a brain monitoring and modulation lead.

FIG. 16 shows a perspective view of a monitoring and modulation lead. In FIG. 16, four stimulation regions on the lead each contain three independent stimulation electrodes. All three stimulation electrodes 36a, 36b, 36c are only visible on the distal-most region. Two stimulating electrodes are visible in the other regions of the lead including 35a, 35b, 34a, 34b, 33a, 33b. Additionally, the lead has three recording electrodes 37, 38 and 39 as well as an additional recording electrode 52 near the distal lead tip 32. An inner shaft 53 is contained within lead body 10 and may be adapted to accommodate guidewires, stylets, lumens, etc. previously described herein.

Figure 17:
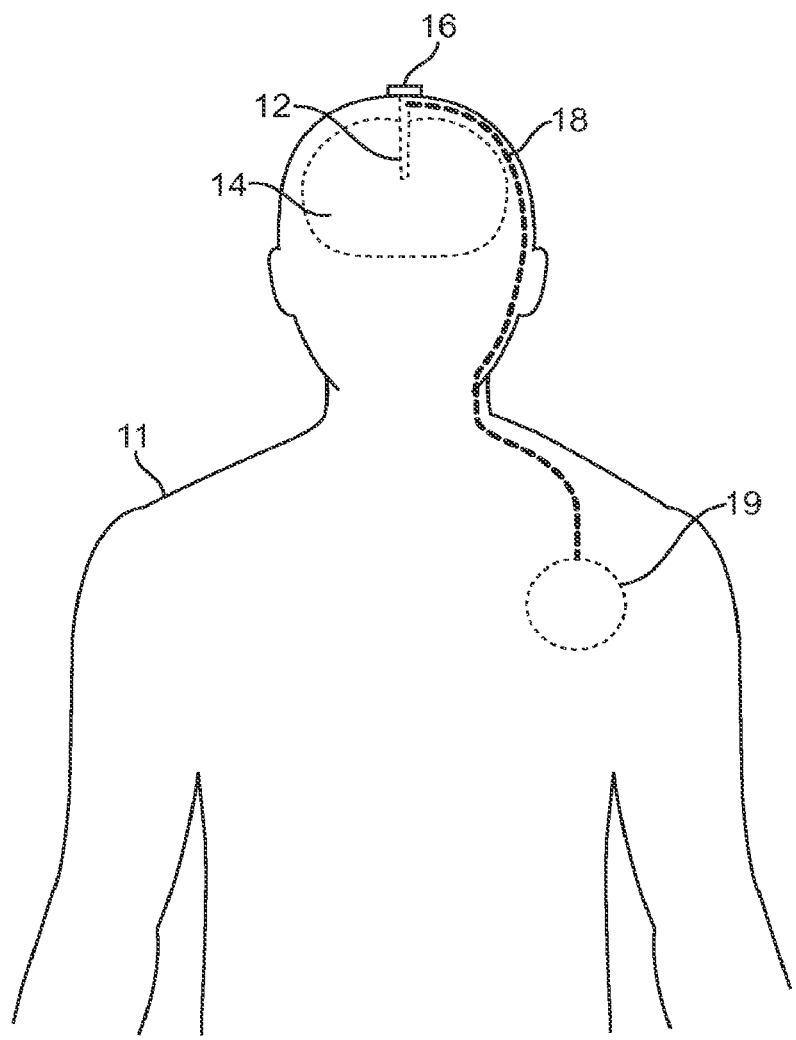
FIG. 17 shows a brain monitoring and modulation lead implanted into a patient's head.

FIG. 17 shows a monitoring and modulating probe or lead 12 secured to the skull of a patient 11 with a fixture 16 and implanted into brain tissue 14. An extension lead 18 couples the probe 12 with a controllable pulse generator 19. The lead often runs under the patient's skin, although it may not and the controllable pulse generator 19 may be implanted or it may remain external to the body of the patient 11. Additional details on a fixture for securing the probe to the skull are disclosed in U.S. Provisional Patent Application No. 60/908, 367 the entire contents of which are incorporated herein by reference.

Table 1 below summarizes data collected that demonstrate that different functional stimulation effects can be achieved by stimulating different stimulation sites around an annular ring. A lead similar to that illustrated in FIG. 16 was inserted into the basal ganglia of an anesthetized cat. The stimulating sites in the most distal annular ring (36a, 36b and 36c) were energized together and independently to electrically stimulate the brain. The ground was placed in the temporalis muscle. Electrical stimulation of sufficient magnitude evoked a response in either the ipsilateral or contralateral or both facial muscles. Stimulation magnitude was delivered in voltage steps, and the motor response was graded on a rank-ordered scale (NR—No Response; THR, Response Threshold; larger numbers correspond to larger magnitude of suprathreshold responses). When site 36a was stimulated alone, the response threshold for ipsilateral movement was lower than for contralateral movement. When site 36b was stimulated alone, the response threshold for ipsilateral and contralateral movement was the same. When site 36c was stimulated alone, the threshold for contralateral movement was lower than for ipsilateral movement. When all three sites were stimulated simultaneously, the threshold for ipsilateral movement was lower than for contralateral movement, but the threshold for both ipsilateral and contralateral movement was lower than with stimulation of any single site. Data from this testing is summarized in Table 1 below, and this pattern of differential stimulation thresholds demonstrates that stimulating different sites within an annular ring steers electrical current within the brain.

Figure 18A:
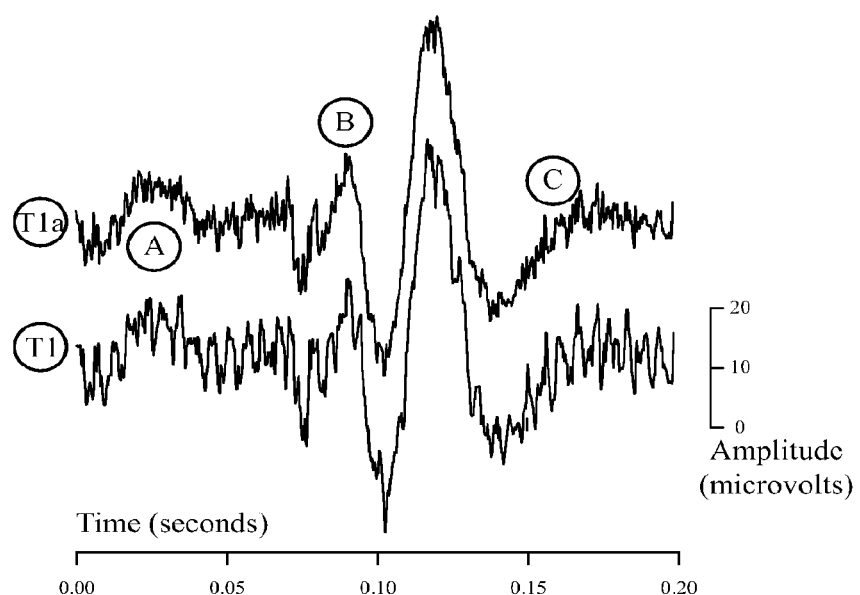
FIGS. 18A-18C show sample recordings of brain electrical potentials from two recording electrodes.
Figure 18B:
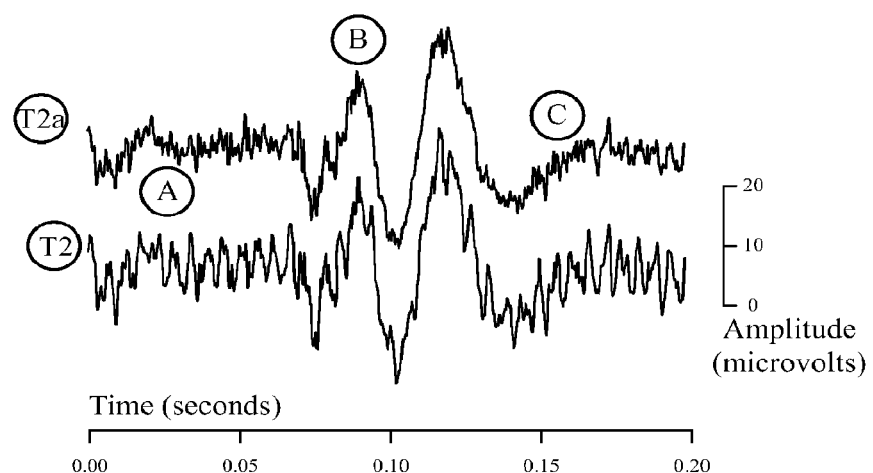
Figure 18C:
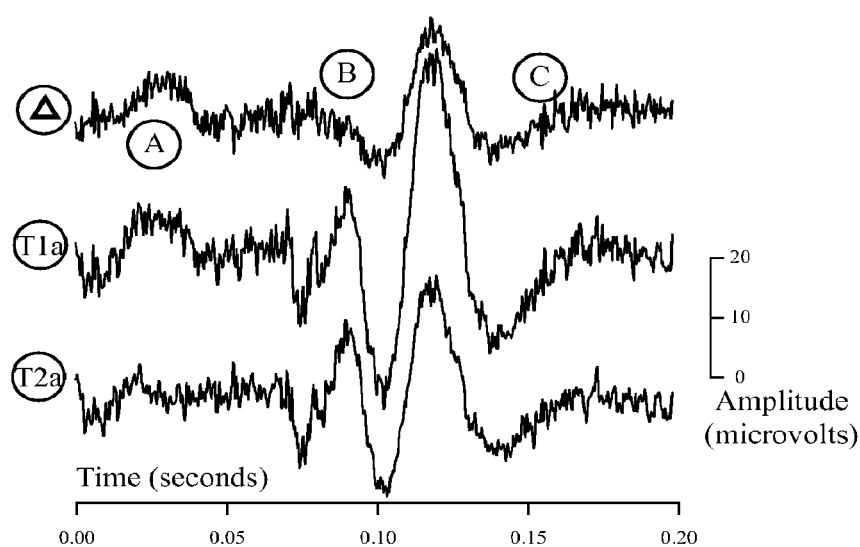

FIGS. 18A-18C demonstrate that the lead can record field potentials, and that different recording sites record different potentials. The recording was obtained from the same lead illustrated in FIG. 16 as discussed above, and with the same placement. The response was evoked by sensory stimulation of the visual pathways by waving a flashlight before the eyes. In FIG. 18A, Trace T1 was recorded from recording site 38, and in FIG. 18B trace T2 was recorded from recording site 39. Spectrum analysis of these traces revealed oscillations at 180 Hz, and 300 Hz, which are believed to result from unintended coupling to the power grid. A Christiano-Fitzgerald filter was applied to remove signal energy near these frequencies, and the filtered traces are denoted T1a and T2a as shown in FIGS. 18A-18C. The trace in FIG. 18C is the arithmetic difference T1a-T2a. The traces look similar, but they are not proportional, as they would be if they resulted principally from electrical cross-talk. At position A, T1/T1a has a more sustained positively compared to T2/T2a. At position B, the positively in traces T1/T1a and T2/T2a are nearly identical. The amplitude of the triphasic wave between positions B and C differs considerably in traces T1/T1a and T2/T2a. The amplitude of this recorded potential is somewhat less than the amplitude of an optimally recorded field potential, reflecting the position of the lead near but not in the optic tract.

Figure 19A:
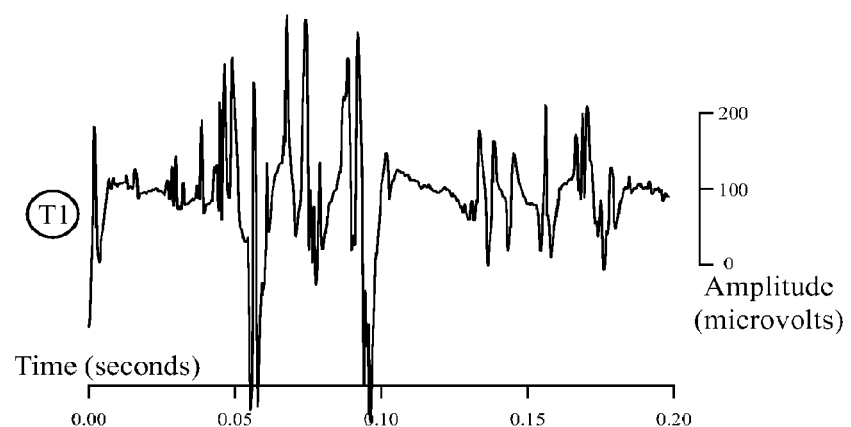
FIGS. 19A-19C show additional sample recordings of brain electrical potentials from two recording electrodes.
Figure 19B:
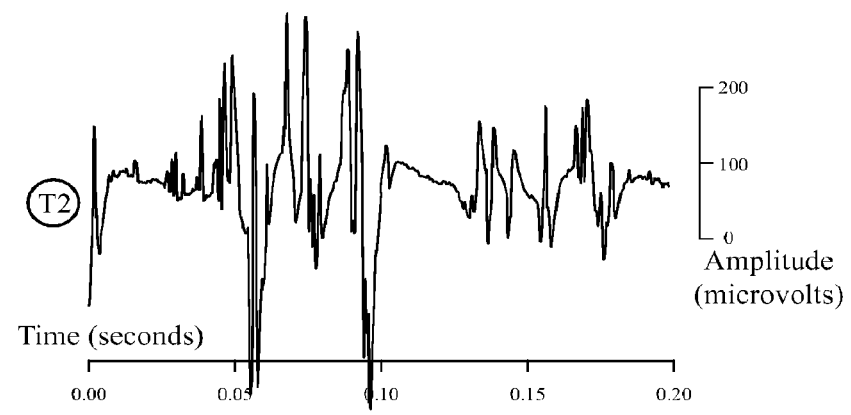
Figure 19C:
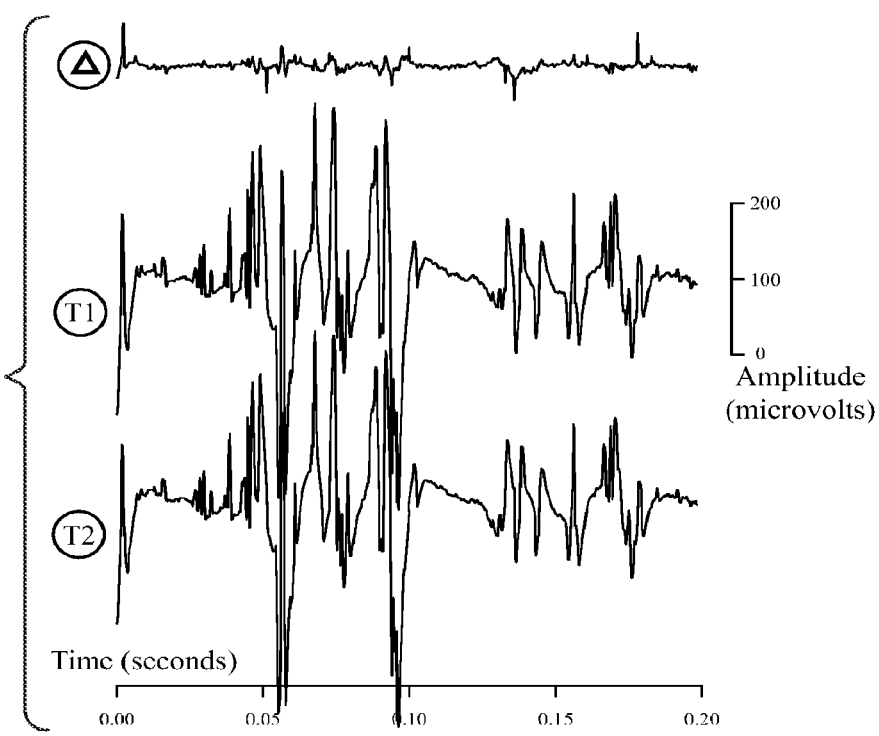

FIGS. 19A-19C demonstrate that the lead can record spontaneous activity field potentials characteristic of placement in a grey matter nucleus. The recording was obtained from a location 3 mm dorsal to the location from which the recording in FIGS. 18A-18C was obtained. Because the amplitude of this recording was much greater than the amplitude of interference from the power grid, Christiano-Fitzgerald filtering was not necessary. Trace T1 in FIG. 19A was recorded from recording site 38, and trace T2 in FIG. 19B was recorded from recording site 39. The trace in FIG. 19C is the arithmetic difference T1-T2. The traces look similar, with a time course and amplitude characteristic of field potential recordings. The difference trace, has several transient waves with duration from 0.5 to 3.5 msec, and amplitude of a few tens of millivolts, characteristic of action potential waveforms. Together with the recording shown in FIGS. 18A-18C, these data demonstrate that a lead such as that illustrated in FIG. 16 can record field potentials from white matter and grey matter, and with suitable signal processing can also record action potential spikes.

| Activate Surfaces | Stimulation (V) | Ipsilateral Facial Muscle Response Grade | Contralateral Facial Muscle Response Grade |
|---|---|---|---|
| 36a, 36b, 36c | 1.0 | NR | NR |
| | 2.0 | NR | NR |
| | 2.2 | THR | NR |
| | 2.6 | 1 | NR |
| | 2.7 | 1 | THR |
| 36a | 1.0 | NR | NR |
| | 2.0 | NR | NR |
| | 3.0 | NR | NR |
| | 3.6 | THR | NR |
| | 4.0 | 1 | NR |
| | 4.3 | 1 | NR |
| | 4.5 | 2 | THR |
| 36b | 1.0 | NR | NR |
| | 2.0 | NR | NR |
| | 2.4 | THR | RHR |
| | 4.0 | 2 | 2 |
| 36c | 1.0 | NR | NR |
| | 2.0 | NR | NR |
| | 3.0 | NR | NR |
| | 3.5 | NR | THR |
| | 4.0 | THR | 1 |
| | 4.5 | 1 | 1 |
| | 5.0 | 2 | 2 |

While the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. An apparatus for stimulating tissue, the apparatus comprising:
an elongate member having a longitudinal axis, a circumference, a proximal end, a distal end, and a central lumen extending between the proximal end and the distal end of the elongate member, the central lumen sized to receive a stylet for advancement of the elongate member slidably thereover;
a plurality of stimulating regions coupled with the elongate member, the stimulating regions arranged along the elongate member and axially spaced apart along the longitudinal axis, the stimulating regions disposed near the distal end, the stimulating regions being adapted to pass current into the tissue, and wherein at least one stimulating region consists of three independent stimulation sites, each of the stimulating sites having one stimulation electrode, the stimulation sites spaced apart from one another and separated from one another by an insulating material, wherein each stimulation site may be stimulated independently of each of the other stimulation sites, wherein the three stimulation sites and the insulating material therebetween are arranged along the circumference of the elongate member to form a closed annular ring, the annular ring adapted to steer a volume of therapeutic electric current into the tissue by the stimulation of one or more of the stimulation electrodes, in order to shape a volume of stimulated tissue;
a single distal electrode disposed at a distalmost end of the elongate member;
an insulating material extending distally from the plurality of stimulating regions to the single distal electrode,
a ring electrode extending around an entirety of the circumference of the elongate member and disposed proximal to at least one of the plurality of stimulating regions;
a first plurality of conductors electrically coupled with the stimulation electrodes;
a plurality of recording electrodes disposed adjacent the stimulating regions, the plurality of recording electrodes adapted to measure local tissue potentials, wherein the ring electrode is one of the recording electrodes; and
a second plurality of conductors electrically coupled with the recording electrodes;
wherein the first plurality of conductors are arranged in one or more groups and the second plurality of conductors are arranged in one or more groups, and wherein the one or more groups of the first plurality of conductors courses separately from the one or more groups of the second plurality of electrodes.

2. The apparatus of claim 1, wherein the first plurality of conductors and the second plurality of conductors are randomly oriented.

3. The apparatus of claim 1, further comprising a multiple contact terminal with at least some of the first plurality of conductors and the second plurality of conductors electrically coupled thereto.

4. The apparatus of claim 1, wherein the first plurality of conductors and the second plurality of conductors course through two separate annular rings.

5. The apparatus of claim 1, further comprising one or more ports near the distal end of the elongate member, the ports in communication with the lumen and adapted to deliver a therapeutic agent to and/or receive a chemical substance from the tissue.

6. The apparatus of claim 5, wherein the one or more ports comprise a gating member.

7. The apparatus of claim 1, wherein the distal electrode is dome-shaped.

8. A method of treating tissue comprising:
providing a lead having at least one stimulating region and a central lumen with a stylet slidably disposed therein;
implanting the lead in tissue, wherein the at least one stimulating region consists of three stimulation sites, each stimulation site having one stimulation electrode, the three stimulation sites arranged in a broken ring separated from one another by an insulator so that each stimulation electrode may be stimulated independently of each of the other stimulation electrodes;
stimulating a volume of tissue with a therapeutic electrical current from a first group of the three stimulation sites; and
steering the therapeutic electrical current through the tissue by independently changing magnitude of the therapeutic electrical current delivered by the first group or by delivering the therapeutic electrical current from a second group of the three stimulation sites different than the first group.

9. The method of claim 8, further comprising measuring tissue responses as a result of stimulating the tissue, with one or more recording electrodes disposed adjacent the at least one stimulating region.

10. The method of claim 9, further comprising:
using a first protocol, when stimulating the volume of tissue, that results in one or more therapeutic effects in the patient; and
using a second protocol, when stimulating the volume of tissue, that provides a more conservative stimulus magnitude relative to the first protocol and just maintains the therapeutic effects, thereby conserving power during the second protocol.

11. The method of claim 10, wherein the conserved power is battery power.

12. The method of claim 10, further comprising:
tracking changes in responses to the stimulation to determine a dynamic range from threshold to saturation in the response to the stimulation as a function of stimulus magnitude.

13. The method of claim 9, wherein measuring local tissue responses comprises collecting chemical substances from the tissue with one or more ports disposed on a distal end of the lead, the ports in fluid communication with the central lumen.

14. The method of claim 13, further comprising stimulating the tissue with a therapeutic agent, the therapeutic agent delivered with at least one of the ports.

15. The method of claim 9, wherein measuring tissue responses comprise measuring local tissue potentials with one or more recording electrodes disposed adjacent the at least one stimulation region.

16. The method of claim 8, wherein the tissue is brain tissue.

17. A method of treating tissue comprising:
providing a lead having at least one stimulating region and a central lumen with a stylet slidably disposed therein;
implanting the lead in tissue, wherein the at least one stimulating region consists of three stimulation sites, each stimulation site having one stimulation electrode, the three stimulation sites arranged in a broken ring separated from one another by an insulator so that each stimulation electrode may be stimulated independently of the other stimulation electrodes;

stimulating a volume of tissue with a therapeutic electrical current from a first group of the three stimulation sites; and steering the therapeutic electrical current through the tissue by independently changing magnitude of the therapeutic electrical current delivered by the first group or by delivering the therapeutic electrical current from a second group of the three stimulation sites different than the first group, wherein steering the electrical current comprises orienting an electric dipole in an orientation in a plane of the broken ring, thereby shaping the volume of the stimulated tissue.

18. The method of claim 17, further comprising improving a tissue modulation capability of the lead, relative to a lead having four or more electrodes, by providing the broken ring with the three independent stimulation sites, each of which is disposed in a different, non-overlapping 120° arc around a circumference of the lead, thereby maximizing the electric dipole that can be produced in more orientations in the plane of the broken ring, as compared to an electric dipole being produced with a lead having four or more electrodes, for a given current density limit.

* * * * *